US008224045B2

(12) United States Patent
Burns et al.

(10) Patent No.: US 8,224,045 B2
(45) Date of Patent: Jul. 17, 2012

(54) SYSTEM FOR EARLY DETECTION OF DENTAL CARIES

(75) Inventors: Peter D. Burns, Fairport, NY (US); Victor C. Wong, Rochester, NY (US); Mark E. Bridges, Spencerport, NY (US); Rongguang Liang, Penfield, NY (US)

(73) Assignee: Carestream Health, Inc., Rochester, NY (US)

( * ) Notice: Subject to any disclaimer, the term of this patent is extended or adjusted under 35 U.S.C. 154(b) by 976 days.

(21) Appl. No.: 11/623,804

(22) Filed: Jan. 17, 2007

(65) Prior Publication Data

US 2008/0170764 A1 Jul. 17, 2008

(51) Int. Cl.
*G06K 9/40* (2006.01)
*G06K 9/00* (2006.01)
*A61C 1/00* (2006.01)

(52) U.S. Cl. .............. 382/128; 382/254; 433/29
(58) Field of Classification Search ........... 382/128, 382/254; 433/29
See application file for complete search history.

(56) References Cited

U.S. PATENT DOCUMENTS

| 3,971,954 A | | 7/1976 | Kleinberg et al. |
| 4,479,499 A | | 10/1984 | Alfano |
| 4,515,476 A | | 5/1985 | Ingmar |
| 5,742,700 A | * | 4/1998 | Yoon et al. ............ 382/132 |
| 5,882,315 A | * | 3/1999 | Ji et al. .................. 600/553 |
| 6,231,338 B1 | | 5/2001 | de Josselin de Jong et al. |
| 6,307,954 B1 | * | 10/2001 | Suzaki ................... 382/117 |
| 6,449,041 B1 | | 9/2002 | Jung et al. |
| 7,102,634 B2 | * | 9/2006 | Kim et al. ............... 345/419 |
| 7,702,139 B2 | * | 4/2010 | Liang et al. ............. 382/128 |
| 2002/0051642 A1 | * | 5/2002 | Hicks .................... 396/429 |
| 2002/0154269 A1 | * | 10/2002 | Liu et al. ................ 351/206 |
| 2004/0202356 A1 | | 10/2004 | Stookey et al. |
| 2004/0240716 A1 | | 12/2004 | de Josselin de Jong et al. |
| 2004/0252303 A1 | * | 12/2004 | Giorgianni et al. ....... 356/402 |
| 2005/0003323 A1 | * | 1/2005 | Katsuda et al. ........... 433/29 |
| 2007/0003164 A1 | * | 1/2007 | Takata et al. ............ 382/284 |

FOREIGN PATENT DOCUMENTS

WO    WO 2007/127036    11/2007

OTHER PUBLICATIONS

E. R. Dougherty; An Introduction to Morphological Image Processing; SPIE Optical Engineering Press, 1992, Ch. 1.
W. K. Pratt; Digital Image Processing; John Wiley and Sons, New York, 1978, pp. 562-566.
G. A. Baxes; Digital Image Processing Principles and Applications; John Wiley, New York, 1994, pp. 91-95.
Thomas Stehle, "Removal of Specular Reflections in Endoscopic Images," ACTA Polytechnica: Journal of Advanced Engineering, vol. 46, No. 4, 2006, pp. 32-36, XP002476869.

* cited by examiner

*Primary Examiner* — Kathleen Y Dulaney

(57) ABSTRACT

A method is disclosed for processing of images to detect dental caries, that includes the following steps. Directing incident light (16) toward a tooth (20), where this light excites a fluorescent emission from the tooth. Obtaining a fluorescence image (35) from the fluorescent light component (19), and obtaining a reflectance image (34) from the back-scattered light (18) from the tooth. Applying a color balance operation to the reflectance image. Removing the specular reflectance components from the color balanced reflectance image (82) to give a back-scattered reflectance image (50). Registering the fluorescent image with the back-scattered reflectance image. Combining the registered fluorescent image (115) with the back-scattered reflectance image to provide a diagnostic image (52).

8 Claims, 5 Drawing Sheets

SYSTEM FOR EARLY DETECTION OF DENTAL CARIES

CROSS REFERENCE TO RELATED APPLICATIONS

Reference is made to commonly-assigned U.S. patent application Ser. No. 11/262,869, filed Oct. 31, 2005, entitled METHOD AND APPARATUS FOR DETECTION OF CARIES, by Wong et al., the disclosure of which is incorporated herein, which issued Sep. 9, 2009 as U.S. Pat. No. 7,596,253.

FIELD OF THE INVENTION

This invention generally relates to a method and apparatus for dental imaging and more particularly to an improved method for early detection of caries using fluorescence and scattering of light.

BACKGROUND OF THE INVENTION

In spite of improvements in detection, treatment, and prevention techniques, dental caries remain a prevalent condition affecting people of all ages. If not properly and promptly treated, caries can lead to permanent tooth damage and even to loss of teeth.

Traditional methods for caries detection include visual examination and tactile probing with a sharp dental explorer device, often assisted by radiographic (x-ray) imaging. Detection using these methods can be somewhat subjective, varying in accuracy due to many factors, including practitioner expertise, location of the infected site, extent of infection, viewing conditions, accuracy of x-ray equipment and processing, and other factors. There are also hazards associated with conventional detection techniques, including the risk of damaging weakened teeth and spreading infection with tactile methods as well as exposure to x-ray radiation. By the time caries are evident under visual and tactile examination, the disease is generally in an advanced stage, requiring a filling and, if not timely treated, possibly leading to tooth loss.

In response to the need for improved caries detection methods, there has been considerable interest in improved imaging techniques that do not employ x-rays. One method that has been commercialized employs fluorescence, caused when teeth are illuminated with high intensity blue light. This technique, termed quantitative light-induced fluorescence (QLF), operates on the principle that sound, healthy tooth enamel yields a higher intensity of fluorescence under excitation from some wavelengths than does de-mineralized enamel that has been damaged by caries infection. The strong correlation between mineral loss and loss of fluorescence for blue light excitation is then used to identify and assess carious areas of the tooth. A different relationship has been found for red light excitation, a region of the spectrum for which bacteria and bacterial by-products in carious regions absorb and fluoresce more pronouncedly than do healthy areas.

Among proposed solutions for optical detection of caries are the following:

U.S. Pat. No. 4,515,476 (Ingmar) discloses use of a laser for providing excitation energy that generates fluorescence at some other wavelength for locating carious areas.

U.S. Pat. No. 6,231,338 (de Josselin de Jong et al.) discloses an imaging apparatus for identifying dental caries using fluorescence detection.

U.S. patent application Publication No. 2004/0240716 (de Josselin de Jong et al.) discloses methods for improved image analysis for images obtained from fluorescing tissue.

U.S. Pat. No. 4,479,499 (Alfano) describes a method for using transillumination to detect caries based on the translucent properties of tooth structure.

Among commercialized products for dental imaging using fluorescence behavior is the QLF Clinical System from Inspektor Research Systems BV, Amsterdam, The Netherlands. Using a different approach, the Diagnodent Laser Caries Detection Aid from KaVo Dental Corporation, Lake Zurich, Ill., detects caries activity monitoring the intensity of fluorescence of bacterial by-products under illumination from red light.

U.S. patent application Publication No. 2004/0202356 (Stookey et al.) describes mathematical processing of spectral changes in fluorescence in order to detect caries in different stages with improved accuracy. Acknowledging the difficulty of early detection when using spectral fluorescence measurements, the '2356 Stookey et al. disclosure describes approaches for enhancing the spectral values obtained, effecting a transformation of the spectral data that is adapted to the spectral response of the camera that obtains the fluorescent image.

While the disclosed methods and apparatus show promise in providing non-invasive, non-ionizing imaging methods for caries detection, there is still room for improvement. One recognized drawback with existing techniques that employ fluorescence imaging relates to image contrast. The image provided by fluorescence generation techniques such as QLF can be difficult to assess due to relatively poor contrast between healthy and infected areas. As noted in the '2356 Stookey et al. disclosure, spectral and intensity changes for incipient caries can be very slight, making it difficult to differentiate non-diseased tooth surface irregularities from incipient caries.

It is well recognized that, with fluorescence techniques, the image contrast that is obtained corresponds to the severity of the condition. Accurate identification of caries using these techniques often requires that the condition be at a more advanced stage, beyond incipient or early caries, because the difference in fluorescence between carious and sound tooth structure is very small for caries at an early stage. In such cases, detection accuracy using fluorescence techniques may not show marked improvement over conventional methods. Because of this shortcoming, the use of fluorescence effects appears to have some practical limits that prevent accurate diagnosis of incipient caries. As a result, a caries condition may continue undetected until it is more serious, requiring a filling.

In order to take advantage of opportunities for non-invasive dental techniques to forestall caries, it is necessary that caries be detected at the onset. In many cases, as is acknowledged in the '2356 Stookey et al. disclosure, this level of detection has been found to be difficult to achieve using existing fluorescence imaging techniques, such as QLF. As a result, early caries can continue undetected, so that by the time positive detection is obtained, the opportunity for reversal using low-cost preventive measures can be lost.

Thus, it can be seen that there is a need for a non-invasive, non-ionizing imaging method for caries detection that offers improved accuracy for detection of caries, particularly in its earlier stages.

SUMMARY OF THE INVENTION

Briefly, according to one aspect of the present invention, a method for processing images to detect dental caries comprising:

(a) directing incident light toward a tooth, wherein the incident light excites a fluorescent emission from the tooth tissue;
(b) obtaining fluorescence image data from the fluorescent emission;
(c) obtaining, from reflected light, reflectance image data from the tooth tissue;
(d) applying color balance to the reflectance image data;
(e) removing specular reflectance from the color balanced image data;
(f) registering the fluorescent image data with the specular reflectance compensated image data; and
(g) combining the registered fluorescent image data with the specular reflectance compensated image data to provide a diagnostic image.

It is a feature of the present invention that it utilizes both fluorescence and reflectance image data for dental imaging.

It is an advantage of the present invention that it offers enhancement over existing fluorescence imaging techniques, useful for detection of caries in its incipient stages.

These and other objects, features, and advantages of the present invention will become apparent to those skilled in the art upon a reading of the following detailed description when taken in conjunction with the drawings wherein there is shown and described an illustrative embodiment of the invention.

DETAILED DESCRIPTION OF THE INVENTION

Figure 1:
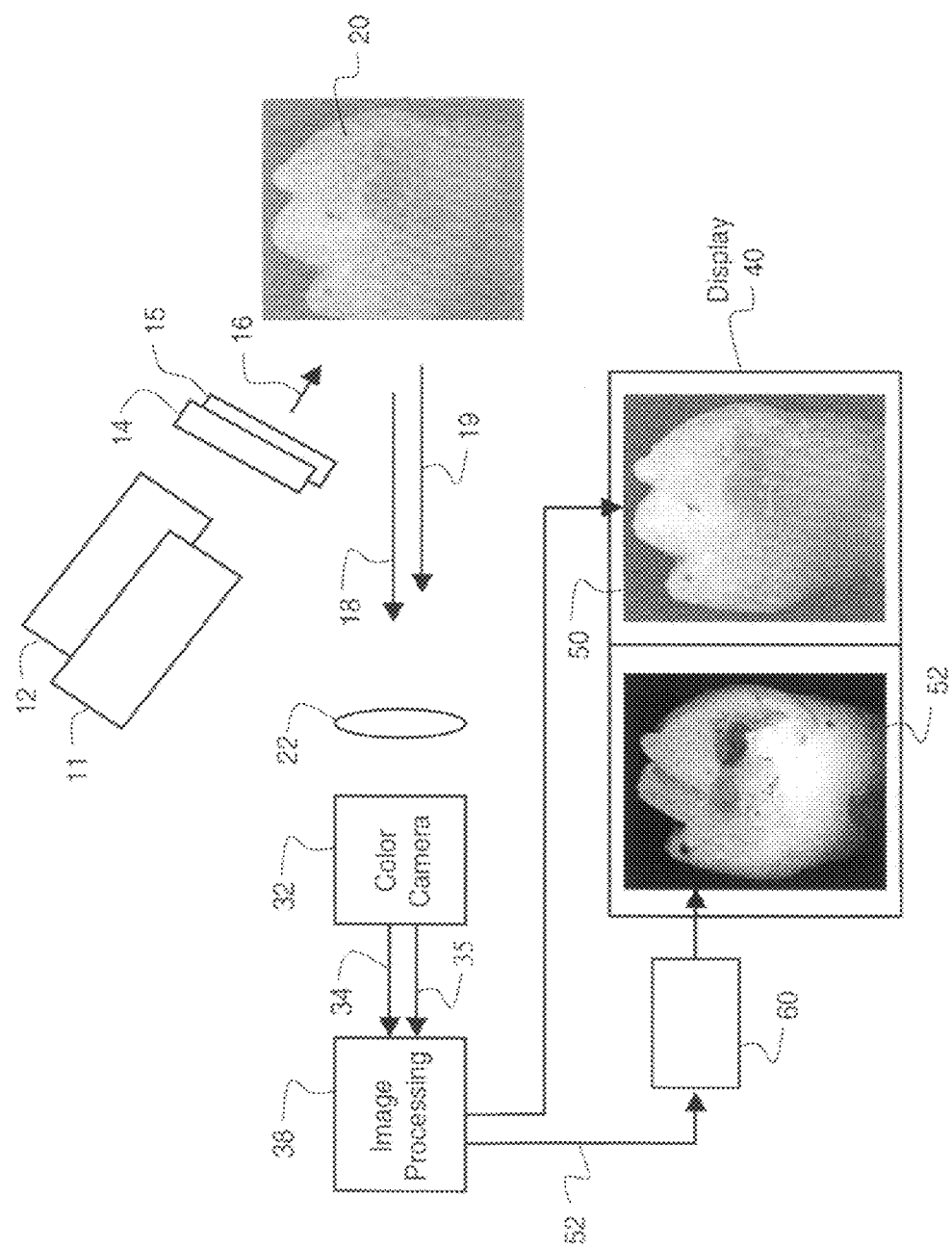
FIG. 1 is a schematic block diagram of an imaging apparatus for caries detection according to one embodiment.

The present description will be directed in particular to elements forming part of, or in cooperation more directly witk the apparatus in accordance with the present invention. It is to be understood that elements not specifically shown or described may take various forms well known to those skilled in the art.

As noted in the preceding background section, it is known that fluorescence can be used to detect dental caries using either of two characteristic responses: First, excitation by a blue light source causes healthy tooth tissue to fluoresce in the green spectrum. Secondly, excitation by a red light source can cause bacterial by-products, such as those indicating caries, to fluoresce in the red spectrum.

In order for an understanding of how light is used in the present invention, it is important to give more precise definition to the terms "reflectance" and "back-scattering" as they are used in biomedical applications in general and, more particularly, in the method and apparatus of the present invention. In broadest optical terminology, reflectance generally denotes the sum total of both specular reflectance and scattered reflectance. (Specular reflection is that component of the excitation light that is reflected by the tooth surface at the same angle as the incident angle.) In many biomedical applications, however, as in the dental application of the present invention, the specular component of reflectance is of no interest and is, instead, generally detrimental to obtaining an image or measurement from a sample. The component of reflectance that is of interest for the present application is from back-scattered light only. Specular reflectance must be blocked or otherwise removed from the imaging path. With this distinction in mind, the term "back-scattered reflectance" is used in the present application to denote the component of reflectance that is of interest. "Back-scattered reflectance" is defined as that component of the excitation light that is elastically back-scattered over a wide range of angles by the illuminated tooth structure. "Reflectance image" data, as this term is used in the present invention, refers to image data obtained from back-scattered reflectance and specular reflectance optical components. In the scientific literature, back-scattered reflectance may also be referred to as back-reflectance or simply as back-scattering. Back-scattered reflectance is at the same wavelength as the excitation light.

It has been shown that light scattering properties differ between healthy and carious dental regions. In particular, back-scattered reflectance of light from an illuminated area can be at measurably different levels for normal versus carious areas. This change in reflectance, taken alone, may not be sufficiently pronounced to be of diagnostic value when considered by itself, since this effect is very slight, although detectable. For more advanced stages of caries, for example, back-scattered reflectance may be less effective an indicator than at earlier stages.

Imaging Apparatus

Referring to FIG. 1, there is shown an imaging apparatus for caries detection using the method in one embodiment. A light source 11 directs an incident light 16, at a blue wavelength range or other suitable wavelength range, toward tooth 20 through an optional lens 14 or other light beam conditioning component. The tooth 20 may be illuminated at a proximal surface or at an occlusal surface. Two components of light are then detected by a digital color camera 32 through a lens 22; a back-scattered light component 18 having the same wavelength as the incident light and having measurable reflectance; and a fluorescent light component 19 that has been excited due to the incident light.

Alternatively, a second light source 12 directs an incident light 16, at a second wavelength range, toward tooth 20 through an optional lens 15 or other light beam-conditioning component. In this case, two components of light are then detected by a digital color camera 32 through a lens 22 corresponding to the response to each of the two light sources. The reflectance image component could be generated from the light from the first source; and a fluorescent light component could be generated from the light from the second source.

Figure 5:
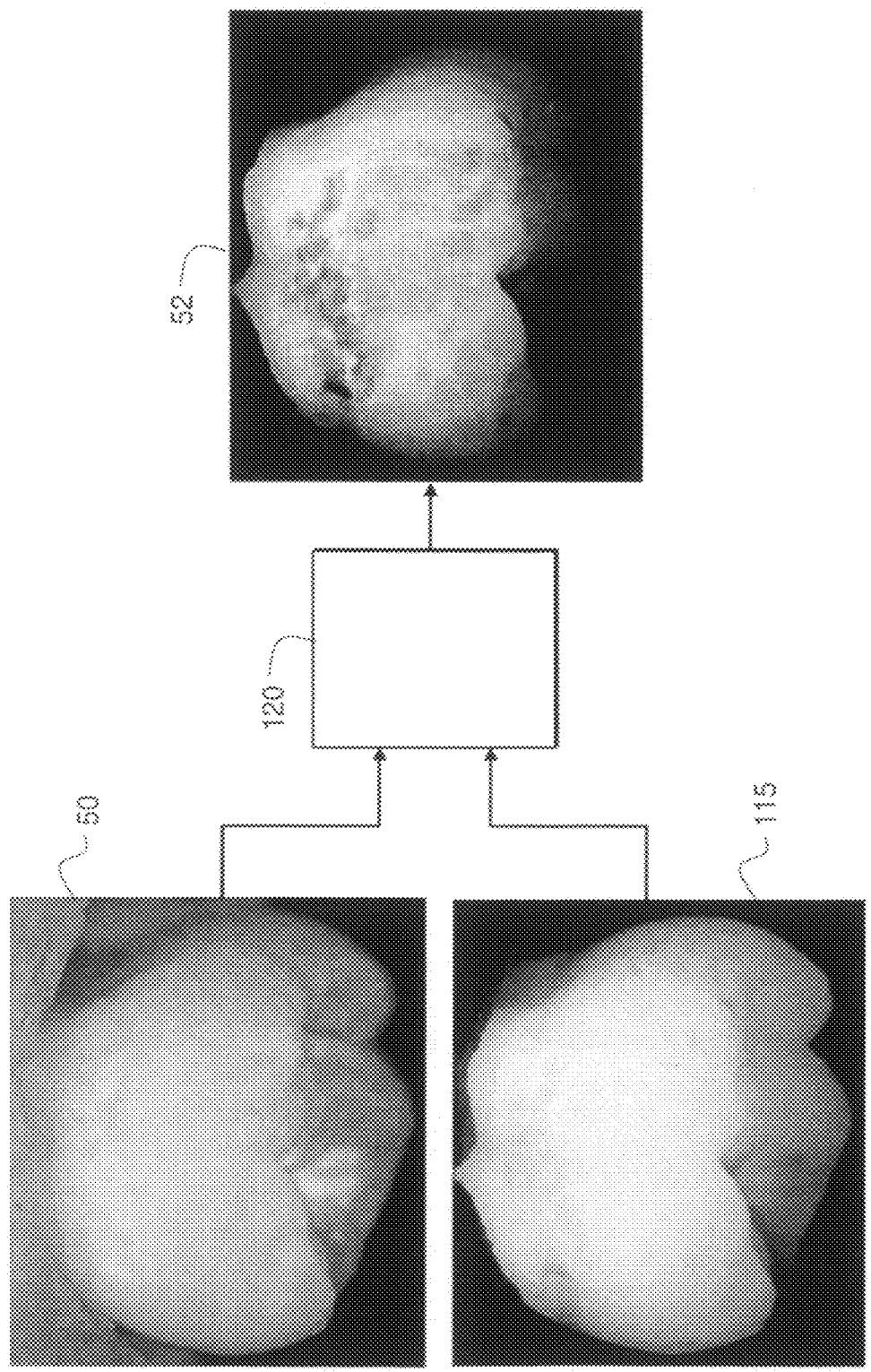
FIG. 5 is a view showing the process for combining dental image data to generate a diagnostic image according to the present invention.

The two corresponding digital color images generated by the digital camera are the reflectance image 34 and fluorescence image 35. These two images are combined by image processing in step 38. The resulting two images, the back-scattered reflectance image, 50, and the diagnostic image, 52, shown in FIG. 5, can then displayed on a computer monitor 40, printed or otherwise presented for interpretation. In FIG. 1, only the back-scattered reflectance image and diagnostic image are shown displayed.

Image Processing

Figure 2:
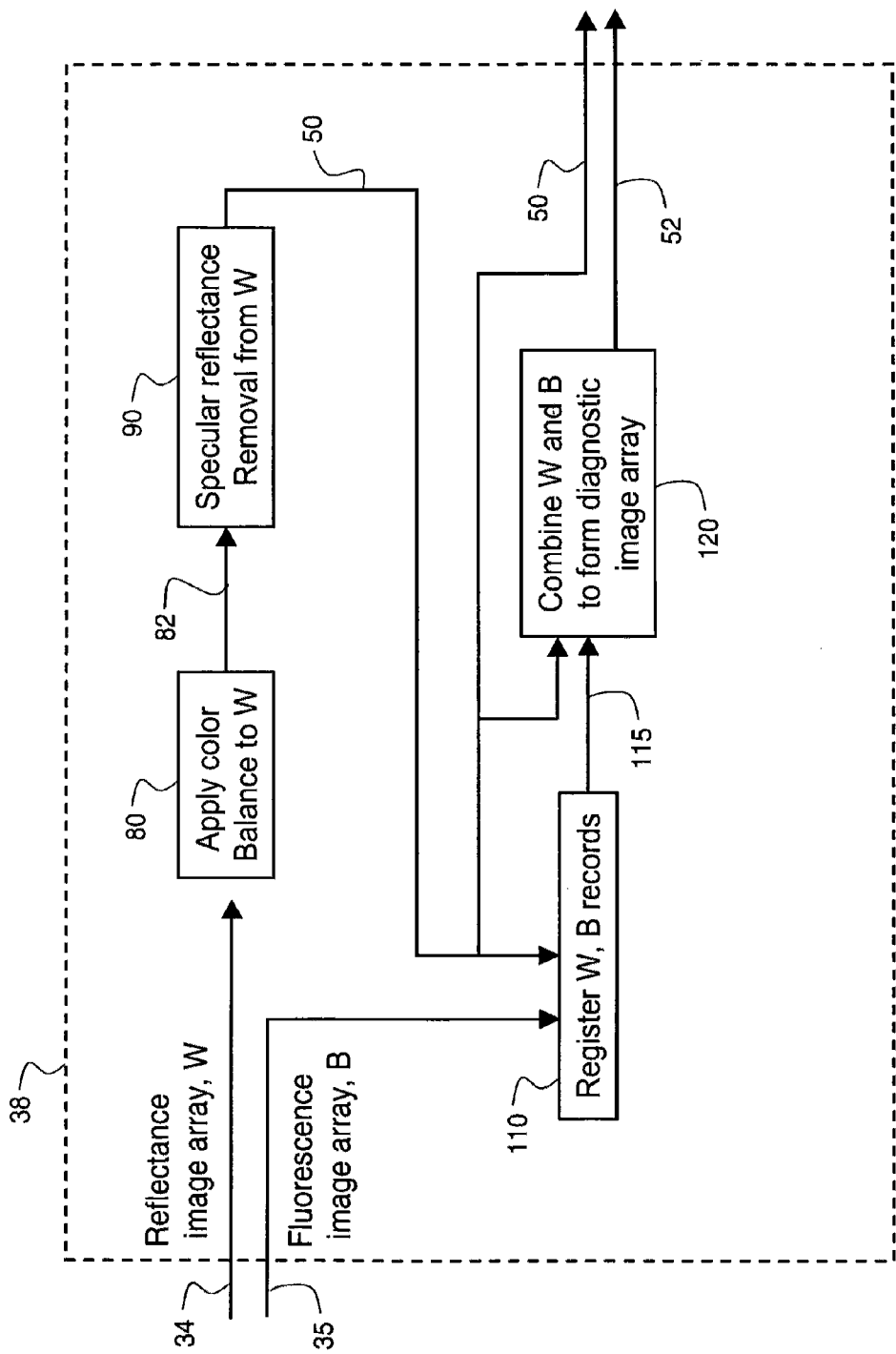
FIG. 2 is a schematic block diagram showing the process for image processing that combines the fluorescence and back-scattered image data to generate a diagnostic image according to the present invention.

Referring to FIG. 2, the two sets of input data to step 38 are the two sets of image array data. Even though the optical elements of the camera and light source may be chosen to minimize the specular reflectance, the reflectance image, 34, contains both back-scattered reflectance and specular reflectance components. The second image 35 contains the fluorescence it image data.

Since the reflectance image will be used both as a component of the final diagnostic image, and for direct viewing, this color image array is first color corrected to compensate for any variation in exposure to the tooth in step 80. A simple embodiment of this step calls for each of the red, green and blue components to be multiplied by a color-specific constant, e.g., 1.05, 1.0, 0.95. The three constants can be chosen such that the resulting color image has a natural color balance when displayed later on a computer monitor. In this case, for example, a gray object near the tooth, would appear gray, rather than with a color cast. The resulting image array is the color balanced reflectance image 82.

Figure 3:
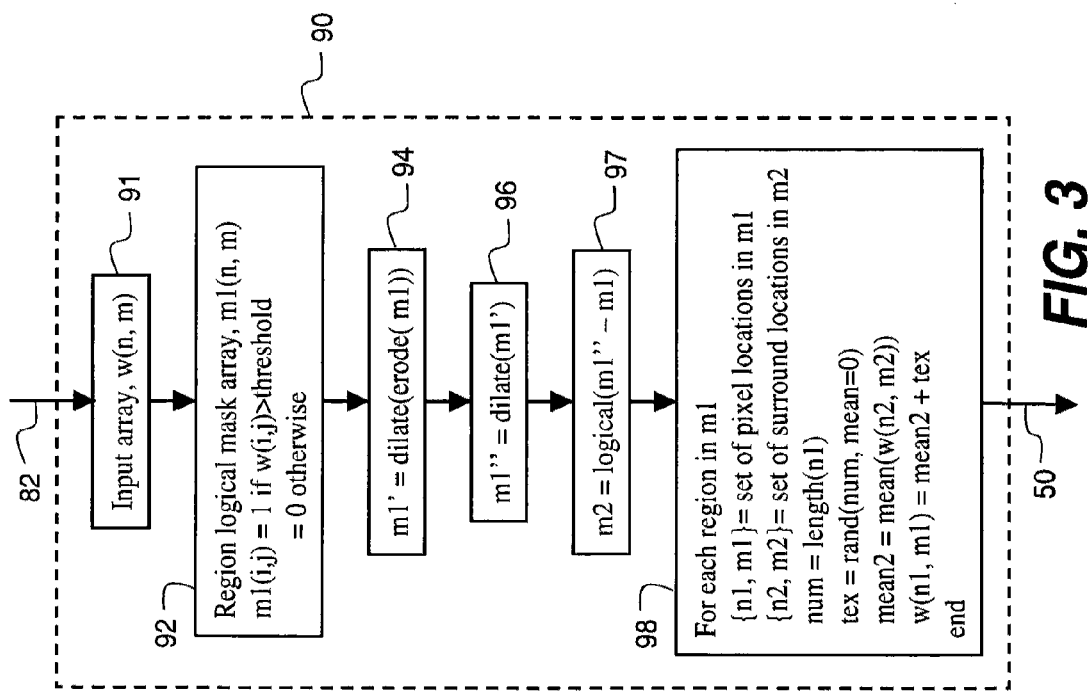
FIG. 3 is a schematic block diagram showing the image processing steps for the removal of specular reflectance image components from the reflectance image data.

As stated above, the specular reflectance component of the back-scattered reflectance image needs to be avoided or removed from the imaging path. When there is an observed or likely specular component in the reflectance image, it can be reduced using the image processing. One embodiment is shown in object 90, specular removal operation. FIG. 3 shows the details. Step 91 indicates the receiving of the color balanced reflectance image which has dimensions, (n lines×m pixels×3; red, green and blue color records). In step 92, several image (pixel) locations of the color balanced reflectance image are identified by selecting those whose values are above a signal threshold, e.g. 90% of the maximum image signal level. This can be done for each color record of the color-balanced reflectance image array, or a single color-record array. The identified pixel locations form a set, or mask array, m1. The thus-identified pixels may form groups of pixels, associated with a specular reflectance region, or be the result of spurious signals. Small regions, i.e., small objects, are eliminated by the morphological operations of erosion, followed by dilation 94. Erosion and dilation are techniques from the field of morphological image processing (E. R. Dougherty, *An Introduction to Morphological Image Processing*, SPIE Optical Engineering Press, Bellingham Washington, USA, 1992, Ch. 1). The result is a logical image array with several contiguous groups of pixels, i.e., specular reflectance regions, identified.

Following this operation, the regions immediately surrounding each of the above specular reflectance regions are identified. The input to this operation is the logical image array mask, m1', from step 94. The operations of morphological dilation 96 and logical pixel-by-pixel subtraction 97 are applied. These result in a logical image array, m2, with only the areas surrounding the specular reflectance regions identified.

For each surround region location in m2, the average pixel value of the corresponding reflectance image is computed in operation 98. This value is then added to the output of a random number generator to generate a series of signal values for each specular reflectance region. The number of random numbers is the same as the number of pixels for each region, m1. The pixel values for each specular reflectance region are then replaced by the set of values for each surrounding region. Thus, each region will have an average value of its surrounding area with the addition of a random texture. This procedure, 98, can also be described using the following steps written as pseudo-code {n1, m1} = sets of pixel locations and corresponding values in m1
{n2, m2 }= sets of surround locations and corresponding values in m2
n = number of contiguous regions
k = a constant
% For each region
For i = 1 to n
num = length(n1(i))
% Generate random texture fluctuations
% rand is a random number generator
tex = k*rand(num, mean = 0)
% Compute surrounding (back-scattered data) value
mean2 = mean( w*m2( n2(i) ) )
% Replace specular reflectance values with back-scattered data
% plus texture
w( n1(i) ) = mean2 + tex
end
% indicates comment about operation on next line
Note that if k=0, no texture signal is added. The output of step 90 is an image with the specular reflectance reduced or removed. This image data is the spectral reflectance compensated color corrected reflectance image, or simply called the back-scattered reflectance image, since it has the specular reflectance component removed.

Figure 4:
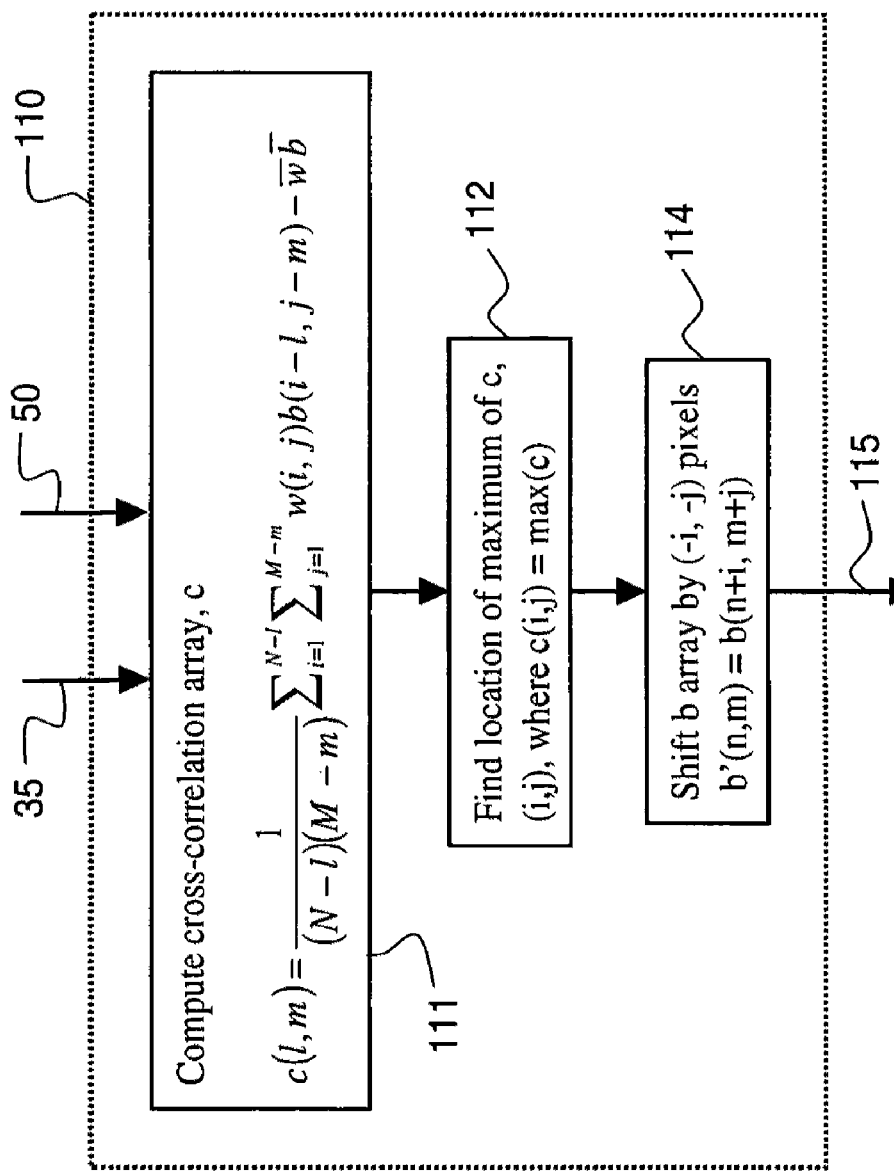
FIG. 4 is a schematic block diagram showing the steps for the spatial registration of the modified reflectance image data, and fluorescence image data arrays.

The next step in the image processing is the spatial registering of the reflectance (w) and fluorescence (b) images. This can be done using a two-dimensional correlation method (W. K. Pratt, *Digital Image Processing*, John Wiley and Sons, New York, pp. 562-566, 1978.), if it is assumed that only a translation correction is needed (and not rotation, etc.). Step 110 shows the procedure. Referring to FIG. 4, first calculate the cross-correlation matrix for the two image data arrays 111, $$c(l, m) = \frac{1}{(N-l)(M-m)} \sum_{i=1}^{N-l} \sum_{j=1}^{M-m} w(i, j)b(i-l, j-m) - \overline{w}\overline{b}$$

where w is the back-scattered reflectance image array and b is the fluorescence image array, and $$\overline{w} = \frac{1}{NM} \sum_{i=1}^{N} \sum_{j=1}^{M} w(i, j),$$

$$\overline{b} = \frac{1}{NM} \sum_{i=1}^{N} \sum_{j=1}^{M} b(i, j)$$

N and M can be either the dimensions of the image data arrays, in pixels, or of corresponding cropped sections thereof. The number of pixels in each direction that two image data array are offset by is found from the location of the maximum of the array c 112. Array b is shifted in the opposite direction in step 114. The result is a shifted fluorescence image data array, F, 115 that is registered with the back-scattered reflectance image data array R.

As described earlier the processing of the modified image data uses both the reflectance and fluorescence image data to generate a final image that can be used to identify carious areas of the tooth. There are a number of alternative processing methods for combining the reflectance and fluorescence image data, step 120, to form the diagnostic image, 52. In one embodiment, this image processing performs the following operation to form the diagnostic image, D, for each pixel:

$$D = (m^*(F_{value} - o))((n^*(R_{value} - p))  \quad (1)$$

where m and n are suitable multipliers (positive coefficients), o and p are constants (positive, negative or zero), and $F_{value}$ and $R_{value}$ are the code values obtained from fluorescence and reflectance image data, respectively. Note that if both o and p are zero, this operation becomes identical to that described by Equation (1) of commonly-assigned U.S. patent application Ser. No. 11/262,869, by Wong et al.

Alternatively, the modified image data could be combined using one-dimensional look-up table (LUT) operations, common in image processing. A LUT operation invokes a discrete signal mapping using a vector. For each pixel location in an input image, the signal value is used as the index into the LUT vector. The value of the LUT vector at that index value is then stored into a modified image, corresponding to the current location in the input image array. Thus equation (1) could written as, $$D = (LUT_F[(F_{value} - o)]) LUT_R[(R_{value} - p)] \quad (2)$$

where $LUT_F$ and $LUT_R$ are vectors, typically of length K, where K is the number of possible discrete levels that $F_{value}$ and $R_{value}$ can take on. If the LUT arrays include the transformation due to the values o and p, then Equation (2) is, $$D = (LUT_F[(F_{value})]) LUT_R[(R_{value})] \quad (3)$$

A fourth way that the modified image data can be combined is in the form of a generalized multivariate transformation, of which Equations (1) and (2) are special cases, $$D = T[(F_{value} - o, R_{value} - p)] \quad (4)$$

where T is a transformation, for example a polynomial, $$T = AF_{value} + BR_{value} + CF_{value}R_{value} + DF^2_{value} \quad (5)$$

A fifth way that the modified image data can be combined is in the form of a multidimensional look-up table.

Referring to FIG. 1, following the above image processing to generate the diagnostic image, it is often desirable to modify these image data for printing, display and examination. Image processing to sharpen the appearance of the diagnostic image can be performed 60, for example, by the application of an image sharpening, or high-pass filtering operation via discrete convolution (G. A. Baxes, *Digital Image Processing Principles and Applications*, John Wiley, New York, 1994, pp. 91-95).

Thus, what is provided is an apparatus and method for caries detection at early and at later stages using combined effects of back-scattered reflectance and fluorescence.

PARTS LIST 11 light source
12 light source
14 lens
15 lens
16 incident light
18 back-scattered light component
19 fluorescent light component
20 tooth
22 lens
32 camera
34 reflectance image
35 fluorescence image
38 images combined
40 display
50 back-scattered reflectance image
52 diagnostic image
60 image sharpening operation
80 color-balance operation
82 color balanced reflectance image
90 specular removal operation
91 receiving color balanced reflectance image
92 select pixels using a threshold
94 erosion-dilation operation
96 dilation
97 logical subtraction
98 replacement of specular-reflectance regions
110 image spatial registration operation
111 cross-correlation
112 selection of maximum correlation
114 array-shifting
115 registered fluorescence image
120 combining reflectance and fluorescence image operation

The invention claimed is:

1. A method for processing images to detect dental caries, said method comprising:
   directing incident light toward a tooth, wherein said incident light excites a fluorescent emission from tissue of said tooth;
   obtaining a fluorescence image from said fluorescent emission;
   obtaining, from reflected light, a reflectance image of said tooth tissue; and
   using a computer to:
      applying color balance to said reflectance image to compensate for variation in exposure of the tooth to the incident light to produce a color balanced reflectance image of the tooth;
      removing specular reflectance from said color balanced reflectance image while leaving back-scattered reflectance, to produce a specular reflectance corrected image of the tooth, said removing comprising: identifying pixels in said color balanced reflectance image, said identified pixels having values above a signal threshold and being associated with specular reflectance regions; removing specular reflectance regions from said identified pixels; identifying regions surrounding said specular reflectance regions; averaging pixel values in said color balanced reflectance image in said surrounding regions; and replacing said specular reflectance regions in said color balanced reflectance image with a signal value including said averaged pixel values;
      registering said fluorescence image with said specular reflectance corrected image; and
      combining said registered fluorescence image with said specular reflectance corrected image to provide a diagnostic image for detecting dental caries.

2. The method of claim 1 further comprising displaying said diagnostic image.

3. The method of claim 1 further comprising sharpening said diagnostic image.

4. The method of claim 1 comprising adding texture to said signal value.

5. The method of claim 1 wherein the step of combining said registered specular reflectance compensated image and said fluorescence image comprises applying an offset value to each image.

6. The method of claim 1 wherein the step of combining said registered specular reflectance compensated image and said fluorescence image comprises applying a polynomial transformation whose inputs values are data sets of the two images.

7. The method of claim 1 wherein the step of combining said specular reflectance corrected image and said fluorescence image comprises applying a multidimensional look-up table whose inputs are data sets of the two images.

8. The method of claim 1 wherein the step of combining said specular reflectance corrected image and said fluorescence image comprises applying a look-up table.

* * * * *